United States Patent [19]

Bilstad et al.

[11] 4,425,116

[45] Jan. 10, 1984

[54] CONTROL SYSTEM FOR FLUID FLOW APPARATUS

[75] Inventors: Arnold C. Bilstad, Deerfield; Richard I. Brown, Northbrook, both of Ill.

[73] Assignee: Baxter Travenol Laboratories, Inc., Deerfield, Ill.

[21] Appl. No.: 347,819

[22] Filed: Feb. 11, 1982

Related U.S. Application Data

[63] Continuation of Ser. No. 139,884, Apr. 14, 1980, abandoned.

[51] Int. Cl.³ ............................................. A61M 5/00
[52] U.S. Cl. .......................................... 604/34; 604/6; 604/19; 251/7; 137/595
[58] Field of Search .................... 222/182, 212, 214; 251/7, 9; 74/568; 137/595, 566; 604/4–6, 30, 32, 34, 246, 248–250, 19, 27–29, 134, 141, 153, 259; 303/50

[56] References Cited

U.S. PATENT DOCUMENTS

| | | | |
|---|---|---|---|
| 868,322 | 10/1907 | Blum | 137/595 |
| 1,427,455 | 8/1922 | Gates . | |
| 1,690,767 | 11/1928 | Bloch . | |
| 2,298,890 | 10/1942 | Leonard . | |
| 2,770,688 | 11/1956 | Johnson . | |
| 2,893,769 | 7/1959 | Deliso . | |
| 2,966,928 | 1/1961 | Fairchild . | |
| 2,986,168 | 5/1961 | Sikula . | |
| 3,063,306 | 11/1962 | Jeffrey | 303/50 |
| 3,245,269 | 4/1966 | Ivie . | |
| 3,359,910 | 12/1967 | Latham, Jr. . | |
| 3,402,853 | 9/1968 | Perl | 251/9 |
| 3,411,534 | 11/1968 | Rose | 604/32 X |
| 3,411,540 | 11/1968 | Iannelli . | |
| 3,438,551 | 4/1969 | Belisle . | |
| 3,489,146 | 1/1970 | Rubin et al. | 604/27 |
| 3,515,170 | 6/1970 | Mullaly . | |
| 3,517,695 | 6/1970 | Eveleigh et al. | 137/566 |
| 3,550,619 | 12/1970 | Halasz et al. | 251/7 |
| 3,570,531 | 3/1971 | McGay . | |
| 3,679,331 | 7/1972 | Kushner . | |
| 3,709,222 | 1/1973 | DeVries | 604/29 X |
| 3,805,842 | 4/1974 | Thompson et al. . | |
| 3,865,134 | 2/1975 | Holcomb . | |
| 3,872,863 | 3/1975 | Lasker et al. | 604/29 |
| 3,912,168 | 10/1975 | Mullins et al. | 604/153 X |
| 3,918,490 | 11/1975 | Goda . | |
| 3,985,134 | 10/1976 | Lissot et al. . | |
| 4,061,142 | 12/1977 | Tuttle | 604/34 |
| 4,096,859 | 6/1978 | Agarwal et al. | 604/29 X |
| 4,131,126 | 12/1978 | Chromik . | |
| 4,190,047 | 2/1980 | Jacobsen et al. | 604/29 X |
| 4,195,631 | 4/1980 | Baucom | 604/6 |
| 4,217,993 | 8/1980 | Jess et al. | 604/153 X |
| 4,236,880 | 12/1980 | Archibald | 604/153 X |
| 4,258,717 | 3/1981 | Bisera et al. | 604/30 X |
| 4,278,085 | 7/1981 | Shim | 604/153 X |
| 4,367,736 | 1/1983 | Gupton | 604/30 |
| 4,380,236 | 4/1983 | Norton | 604/32 X |

FOREIGN PATENT DOCUMENTS

| | | |
|---|---|---|
| 3306000 | 8/1974 | Fed. Rep. of Germany . |
| 2700491 | 5/1977 | Fed. Rep. of Germany ......... 251/7 |

Primary Examiner—C. Fred Rosenbaum
Assistant Examiner—Michelle N. Lester
Attorney, Agent, or Firm—Paul C. Flattery; Garrettson Ellis; Daniel D. Ryan

[57] ABSTRACT

A flow control system, for example for blood plasma or other medical fluids, comprises a plurality of flexible, collapsible flow conduits for the selective and aseptic transfer of fluids between various locations through said conduits. Switching means are provided for selectively collapsing a plurality of separate sections of the conduit to block fluid flow therethrough, to selectively define specific and variable fluid flow paths in the flow conduit. In accordance with this invention, the switching means defines a cam plate, which in turn defines a generally flat face positioned adjacent portions of the flow conduit. Pivot means are provided causing the cam plate to be rotatable about an axis normal to the flat face. Also, a cam connecting system is disclosed, to adapt it to pass through an openable door.

29 Claims, 7 Drawing Figures

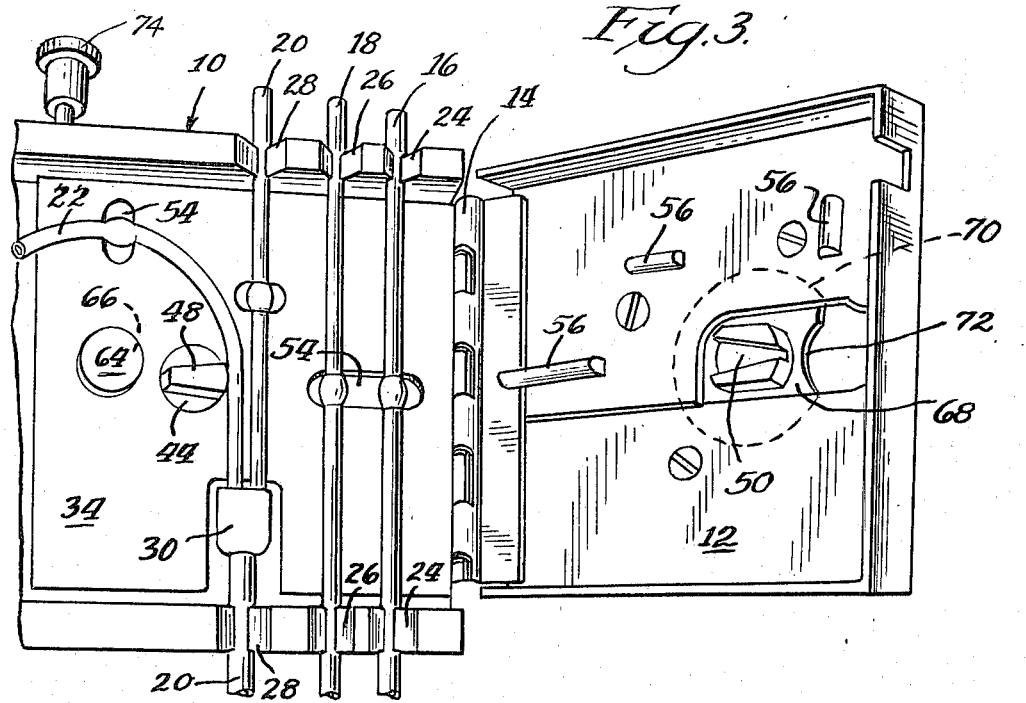
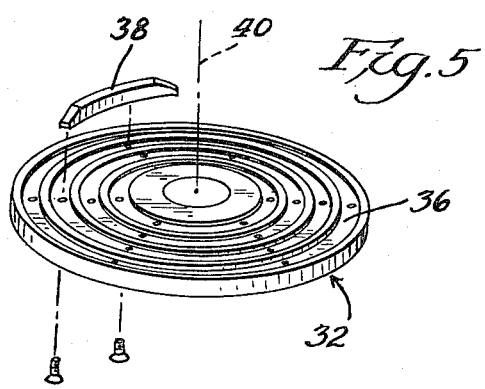
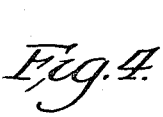
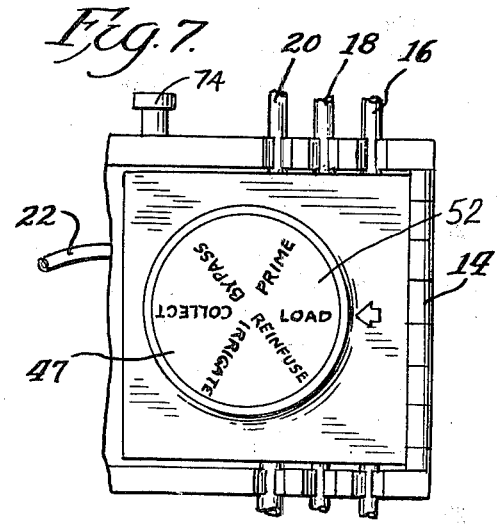

CONTROL SYSTEM FOR FLUID FLOW APPARATUS

This is a continuation of application Ser. No. 139,884, filed Apr. 14, 1980 now abandoned.

BACKGROUND OF THE INVENTION

This application relates to a simple manual control system, for providing control to a fluid flow apparatus which typically performs a relatively complex series of fluid switching functions through multiple flow paths. Additionally, the control system of this invention can simultaneously control the electrical functions of the same apparatus, in correlation with the fluid flow functions, from a single control knob.

The requirements of greater efficiency and cost reduction throughout all of technology, and specifically in the medical field, are resulting in the development of the relatively automated apparatus such as for the processing of blood or blood components, or for analysis of medical or other fluids. Such apparatus may be used in hemodialysis, blood oxygenation, or blood collection and component separation, including plasmapheresis.

In Sikula U.S. Pat. No. 2,986,168, a control valve is shown for controlling fluid flow through a pair of valving elements as disposed in a single body.

In Gates U.S. Pat. No. 1,427,455, cam operated valves control multiple flexible flow passages by compressing them to close, and by releasing them to open.

Bloch U.S. Pat. No. 1,690,767 discloses another type of delivery valve in which cams on a rotatable member open and close a pair of valves.

However, a need remains for a control system which is capable of separately and independently controlling the flow from a single control member through multiple flow paths, while at the same time optionally providing correlated electrical controls. Furthermore, in accordance with this invention, a control member may be mounted on a door or other separable member of the apparatus, with means being provided so that the connection of the control knob to the controlled elements may be disconnected and reconnected in a manner which does not permit disruption of the correlation of the position of the control knob with the controlled elements.

DESCRIPTION OF THE INVENTION

In accordance with this invention, switching means are provided for a flow system comprising a plurality of flexible, collapsible flow conduits for the selective transfer of fluid through the conduit. The switching means is adapted for selectively collapsing a plurality of separate sections of the conduit to block fluid flow through them, for the purpose of selectively defining specific variable fluid flow paths in the flow conduits.

In accordance with this invention, the switching means defines a cam plate defining a generally flat face, positioned adjacent portions of the flow conduits. Pivot means are provided, causing the cam plate to be rotatable about an axis normal to the flat face. Cam members are carried on the flat face, with the cam members preferably defining differing radii from the axis, for the purpose of permitting separate and independent control of a plurality of flow conduits.

The cam members are positioned to cause the pressurized collapse of a portion of the flow conduits, to block fluid flow through such portion when the cam plate is in one rotational position, and to be disengaged in another rotational position from the pressurized, collapsed relation caused by the cam member, to permit flow through the portion when the cam plate is in the other rotational position.

Accordingly, by this invention, a versatile, independent control of a plurality of flow conduits is provided. Multiple cam members may be placed at the same radii from the axis, if it is desired to close and open a specific flow conduit more than once during a process cycle, with the cycle control being typically governed by a single 360° rotation of the cam plate. Accordingly, any desired pattern of flow modes may be defined in the plurality of flow conduits as the cam plate is rotated about its axis.

Preferably, the cam members are arcuate in shape, each cam member defining a generally constant radius about the axis. Also, the flexible, collapsible flow conduits are typically positioned in interconnecting relation with a plurality of containers, and may also include conduit means for communicating with the venous system of a blood donor, for example, to provide a blood processing apparatus such as plasmapheresis apparatus, having multiple phases or cycles of operation as defined by the position of the cam plate.

Shaft means typically connect the cam plate with a control knob, with the shaft means optionally defining a pair of separable members to permit mechanical connection and disconnection of the cam plate and control knob by separation of the separable members. The separable members define shaped, mating portions at facing ends, permitting the connection of the shaft means by joining of the separable members only when the separable members occupy one specific relative rotational position. Accordingly, reconnection of the shaft means for operation of the control means is not possible unless the control knob is in proper rotational orientation with respect to the cam plate. Indicia may be placed in association with the control knob to show the mode of operation that the system is currently in.

The shaft means may also connect with and operate rotary switch means, which may constitute a control for an electrical system utilized in the device. Accordingly, the electrical functions controlled by the rotary switch means, the fluid flow functions controlled by the cam plate, and the rotational position of the control knob are all correlated on the shaft means when it is in the controlled position.

The separable members of the shaft are typically utilized by placing one of the separable members and the control knob on a door member, which is hingedly attached to a housing for the remainder of the flow system. Thus, the door member may be opened, resulting in disconnection between the cam plate and the control knob, for access to the interior of the device, particularly the flexible conduits, which may be intended for one time use. When the device has been properly loaded and ready for operation, the door member may be closed, which can ony take place through connection of the shaped, mating portions of the separable members when in proper relative rotational position, indicating proper rotational correlation of the cam plate and control knob.

In the drawings,

FIG. 3 is a perspective view of the apparatus of FIG. 1 showing its interior, with the door member in its open position.

FIG. 4 is a truth table, illustrating the positions of closure valves of FIGS. 1 and 2 during the six modes of operation of the specific plasmapheresis device.

FIG. 5 is a fragmentary, perspective view of a cam plate used in this invention, illustrating how the arcuate cam members may be attached to the cam plate to define arcs of generally constant radius about the axis of rotation.

FIG. 6 is a fragmentary, enlarged longitudinal sectional view of a portion of FIG. 2, showing a valve assembly in a position closing flow through a flexible, collapsible flow conduit.

FIG. 7 is a fragmentary, elevational view showing a portion of the front face of the door assembly in closed position, and showing the control knob carried by the door member.

Figure 1:
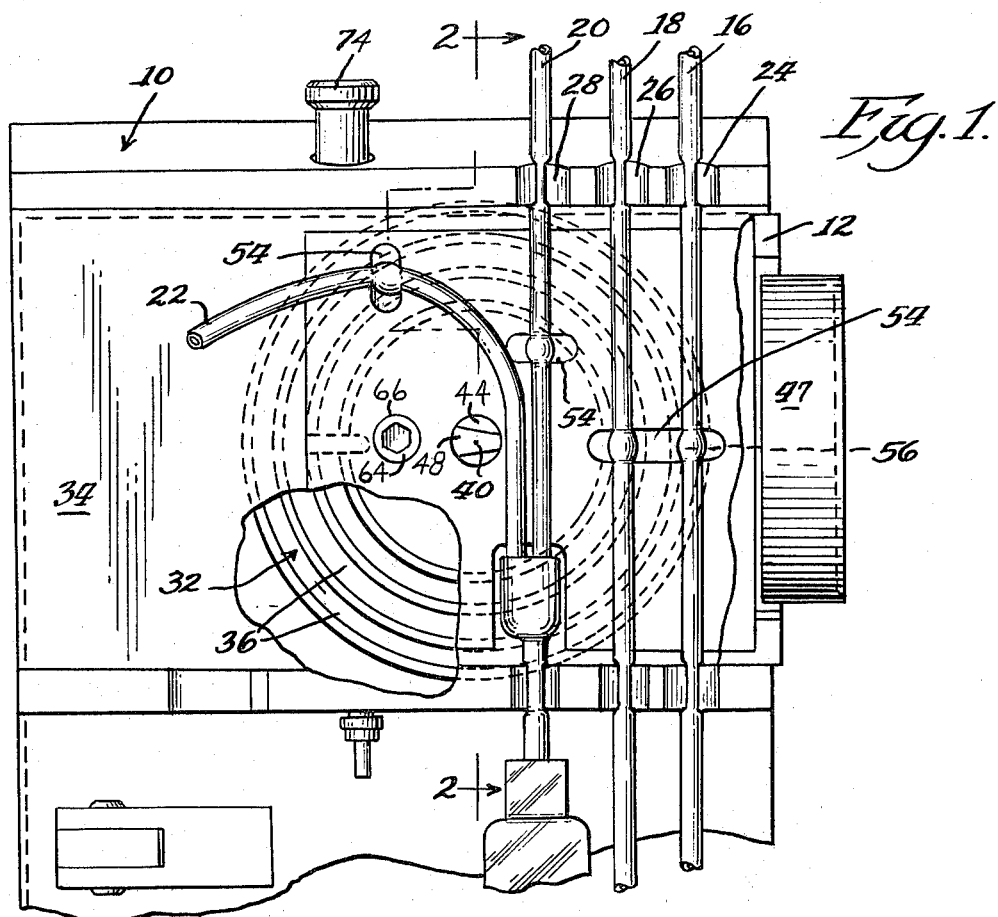
FIG. 1 is an elevational view, with portions broken away, of a control switch assembly for a flow system in an electrically operated plasmapheresis apparatus, with the door member associated with the assembly shown in its open position.

Referring to the drawings, a flow control system is disclosed which may be utilized as part of any apparatus for controlling fluid flow, and including correlated control means for an electrical system for the same apparatus. Specifically, the flow control system disclosed may be utilized as part of a plasmapheresis apparatus as described in the application of Richard I. Brown, et al. filed concurrently herewith and entitled "Blood Fractionation Apparatus" Ser. No. 140,111.

Housing 10 may carry the flow control apparatus of this invention. Door member 12 is attached by hinges 14 to housing 10.

A plurality of flexible, collapsible flow conduits 16, 18, 20 and 22 are shown to be positioned in corresponding slots 24, 26, 28 for receiving the respective flexible, collapsible flow conduits. The flow conduits may be part of a disposable set or sets for the handling of blood plasma amd saline solution during the operation of the plasmapheresis device.

For example, flexible conduit 16 may communicate at the top with a first source of saline parenteral solution, and at the bottom with the remainder of the flow circuits of the plasmapheresis apparatus.

Flexible conduit 18 may communicate at its top with a second source of saline, parenteral solution, and at the bottom with the remainder of the flow circuits.

Flow conduit 20 may communicate at its top with an empty container for collecting plasma extracted from whole blood by the plasmapheresis device, and at its bottom communicating with an enlarged, flexible chamber, as part of a disposable set which fits into a blood detection device, and which also connects with the remainder of the flow conduits.

Conduit 22 communicates at one end with conduit 20 through Y-connection chamber 30, as part of the disposable set, and leads at its other end to a bypass plasma line for returning plasma to the donor.

Other flexible disposable flow lines in the specific plasmapheresis set are not directly governed by the switching mechanism of this invention, as described in the patent application cited above.

In accordance with this invention, switching means are provided including a cam plate 32, positioned behind wall 34 of housing 10. Cam plate 32 defines a generally flat face 35 which, in turn, may define a series of concentric, annular grooves 36 for receiving separate, preferably generally arcuate cam members 38, 38a positioned in grooves 36, to define arcs of generally constant radii of about the axis of rotation 40 of the cam plate.

The pivoting means of cam plate 32 is provided by rotatable shaft means 42. Shaft means 42 defines a pair of separable members 44, 46 to permit mechanical connection and disconnection of the cam plate 32 and control knob 47.

As shown in FIG. 3, separate members 44, 46 define at their facing ends, shaped, mating portions 48, 50, permitting the connection of shaft means 42 by joining of the separable members 44, 46 only when the separable members occupy one specific relative rotational position.

For example, as shown in FIG. 3, shaped mating portion 50 defines a generally V-shaped groove, while mating portion 48 is a projection from the end of member 44 shaped to fit within the V-shaped groove 50. Accordingly, only when separable members 44, 46 of shaft 42 are in their relative rotational positions as shown in FIG. 3 can they enter into the engaged relationship shown in FIG. 2, with door member 12 being closed.

Accordingly, it becomes possible in accordance with this invention to open door member 12, thus separating the separable members 44, 46. Flexible conduits may be installed, replaced, or adjusted, and when operation of the apparatus is desired, the door member 12 may be closed again. If control knob 48 is in its proper rotational position relative to cam plate 32, members 44, 46 will interengage, and the door 12 can be successfully closed. Otherwise, the members 44, 46 cannot interengage, and the door cannot be closed.

Accordingly, in all circumstances when door 12 is closed, the indicia 52, associated with knob 47 (see FIG. 7) and indicating the mode of operation that the flow control system is imposing, will always be correct relative to cam plate 32.

As cam plate 32 occupies differing rotational positions, cams 38, which are attached in predetermined positions within grooves 36 of cam plate 32, occupy differing radii from the axis of rotation 40, depending upon the specific annular groove 36 that they occupy. Two separate cams 38, 38a are shown in FIG. 2 to occupy differing radii from axis 40.

As shown in FIGS. 1 and 3, apertures 54 are provided in wall 34 of housing 10. Anvil members 56 are positioned on the inside of door member 12 so that they project to a position immediately adjacent apertures 54. Flexible conduits 16, 18, 20, 22 each project across an aperture 54 and an anvil 56 positioned in or immediately adjacent a corresponding aperture 54.

It can be seen that the points where each flexible conduit crosses an aperture 54 are positioned at a different radius from rotational axis 40 so that each cam or cams 38, as the case may be, occupying a particular annular groove 36, interacts only with a single one of conduits 16, 18, 20 or 22. As shown in FIG. 6, cam 38a for example, at the proper rotational position of cam plate 32, engages plunger 57 to, in the specific instance of FIG. 6, depress it and squeeze conduit 22 into a closed, flow-blocking position. Corresponding plungers are provided to pass through the other apertures 54 to compress the respective conduits 16, 18, 20 against an anvil 56, when impelled by a cam 38 rotated into engaging relation by cam plate 32.

Figure 2:
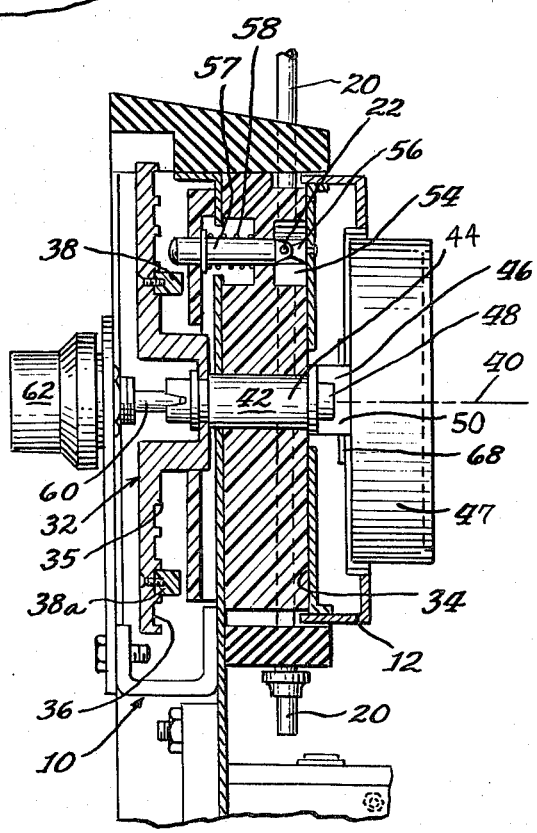
FIG. 2 is a sectional view taken along line 2—2 of FIG. 1, with the door member shown in its closed position.

However, as shown in FIG. 2, when plunger 57 is not engaged by cam 38a, due to a different rotational position of cam plate 32, it is retracted by spring 58 to allow conduit 22 to open, with similar structure and function being utilized in the other plungers 57 as well.

FIG. 4 illustrates a truth table which shows a typical mode of valving operation in the six different valving modes provided in the specific embodiment of the flow control system of this invention. The six modes are as indicated on knob 47, with the system being shown in the "load" mode in FIG. 7.

Turning to the truth table of FIG. 4, the symbol "0" indicates an open position and "1" indicates a closed position. It can be seen that in this rotational position of knob 47 and cam plate 32 all of the valves are open, with each plunger 57 being in its retracted position, permitting flow through all of the tubes 16, 18, 20 and 22.

In the next mode, which involves the priming of the apparatus, a cam 38 moves into engagement with the plunger 57 which controls flow through flexible conduit 20 to close flow through that line.

In the next or bypass mode, cam plate 32 rotates to close conduits 16 and 18, while conduit 20 remains closed.

In the next or "collect" mode, the cam plate 32 is rotated to bring cams 38 into engagement with plungers 57 to close off the conduit 22, while conduit 20 is opened, for collecting the plasma in a sterile container. Conduits 16 and 18 remain closed.

Following this, in the "irrigate mode", cam plate 32 is rotated to close conduits 20 and 22, while the saline source conduits 16, 18 are opened.

Finally, in the "reinfuse" mode, cam plate 32 is rotated to close only conduit 20, so that a flow path leads through conduit 22 for reinfusion of plasma to the donor.

Shaft member 42 communicates as shown in FIG. 2 with shaft extension 60, with a connection which does not permit relative rotation between extension 60 and the rest of shaft 42. Shaft extension 60, in turn, communicates with rotary switch 62, of conventional design, to provide appropriate multiple switching modes to the electrical components of the plasmapheresis device in a manner which correlates with the rotational position of cam plate 32 and knob 47. Accordingly, the necessary electrical functions involving the starting and stopping of roller pumps to impel liquids through the flexible conduits, and the like, is coordinated with the operation of cams 38 in opening and closing flow through flexible conduits 16, 18, 20 and 22, for correlated operation of the various components of the plasmapheresis apparatus through one manual control, which is operated by the user by the manipulation of knob 47. Rotary switch 62 may be connected to any desired number of leads which, in turn, connect to the electrically operated parts of the plasmapheresis device.

Door 12 is selectively latched so that it can only open in the "load" mode as indicated by knob 47, as follows. Projection 64, carried by wall 34 of housing 1, defines a latching groove 66 about at least a portion of its periphery.

Positioned on separable member 46 of shaft 42, behind knob 47, is disc member 68, defining a generally circular periphery 70 about the majority of its periphery, and further defining a cutaway portion 72 at one portion of its periphery. When door member 12 is closed, and knob 47 is positioned in a mode other than "load", for example, the periphery 70 of disc member 68 engages locking groove 66, thus preventing opening of the door. However, when knob member 47 is in the "load" mode, cutaway portion 72 is positioned adjacent projecting member 64 so that there is no engagement of disc 68 in groove 66, and the door is unlatched for opening.

Added manual safety latch 74 is also provided to hold door 12 in locked position.

Accordingly, a flow control system in accordance with this invention is provided which permits complex and multiple valving functions throughout a plurality of flow modes, while at the same time providing simultaneous, correlated electrical switching for operation of the electrical components of a system. Similarly, the control knob for this system may be mounted on a door so as to be separable from the remainder of the system, but may be reliably brought back into connection upon closing of the door without rotational misalignment of the control knob.

The above has been offered for illustrative purposes only, and is not intended to limit the invention of this application, which is as defined in the claims below.

That which is claimed is:

1. A device for controlling the flow of fluid through flexible collapsible conduit means, said device comprising a housing including spaced sidewalls defining an interior area having an access opening, an interior wall extending in said interior area having a front surface facing said access opening and a rear surface facing away from said access opening, slot means for releasably securing a portion of the conduit means in a predetermined configuration along said front interior wall surface, and a door movable between an open position permitting access through said access opening into said interior area to secure the conduit means on said slot means or to remove the conduit means from said slot means and a closed position blocking said access opening and sandwiching the secured conduit means between said front interior wall surface and the interior of said door, fluid control means carried along said rear surface of said interior wall and being movable through a range of positions and operative, when said door is in said closed position, for selectively pressing against and collapsing the conduit means secured in said predetermined configuration along said front surface of said interior wall, thereby effecting the flow of fluid through the conduit means, control handle means carried on the exterior of said door and being operative for movement through a range of positions generally correlated with said range of positions of said fluid control means, and linkage means operative, when said fluid control means and said control handle means are each respectively positioned at generally the same relative correlated position within said respective range of positions, for releasable connecting said control handle means with said fluid control means in response to movement of said door into said closed position and, after said releasable connection has been made and said door is maintained in said closed position, for moving said fluid control means through its range of positions in response to and in relative correlation with movement of said control handle means through its range of positions.

2. A device according to claim 1 wherein said fluid control means includes plate means disposed along said rear interior wall surface, said plate means being operative for rotation relative to said interior wall through said range of positions associated with said fluid control means, pin means extending through said interior wall intermediate said plate means and the conduit means secured in said predetermined configuration along said front interior wall surface, said pin means being movable between a normal position and a displaced position, said pin means being operative during said movement from said normal position toward said displaced position for pressing against and collapsing a area of the conduit means secured in said predetermined configuration along said front interior wall surface to effect the flow of fluid therethrough, and cam means attachable to said plate means to operatively connect said plate means with said pin means for moving said pin means between said normal and displaced positions in response to rotation of said plate means within said associated range of positions, and wherein said linkage means is operative for releasably connecting said control handle means with said plate means and for thereafter transmitting movement of said control handle means into rotation of said plate means in relative correlation with said movement of said control handle means.

3. A device according to claim 2
wherein said cam means includes a generally arcuately shaped cam member attachable to said plate means at a position radially outwardly spaced from the axis of rotation thereof to thereby move in a generally arcuate path during rotation of said plate means, and wherein said pin means is disposed along said path of arcuate movement of said cam member for contact with said cam member during said rotation of said plate means.

4. A device according to claim 3
wherein said plate means includes a plurality of arcuate grooves concentrically arranged at radially spaced intervals outwardly of the axis of rotation of said plate means, each of said grooves accommodating at least one of said cam members, and wherein said pin means includes at least one pin member associated with each of said cam members which are arcuately carried on said plate means, each of said pin members being disposed along said path of arcuate movement of said associated cam member and independently movable in response to contact by said associated cam member between said normal and displaced positions to obstruct the flow of fluid through the conduit means.

5. A device according to claim 2 or 3 or 4
wherein said control handle means includes a control knob disposed on said exterior of said door and rotatable through said range of positions associated with said control handle means, and wherein said linkage means is operative for releasably connecting said control knob with said plate means and for thereafter transmitting rotation of said control knob into correlated rotation of said plate means.

6. A device according to claim 5
wherein said linkage means includes
first shaft means operatively connected with said plate means for common rotation therewith, and
second shaft means operatively connected with said control knob for common rotation therewith, and
means on said first and second shaft means operative, when said plate means and said control knob are each respectively positioned at generally said same relative correlated position, for releasably connecting said first shaft means and said second shaft means in response to movement of said door into said closed position and for thereafter moving said plate means in response to and in relative correlation with movement of said control knob.

7. A device according to claim 6
wherein said linkage means includes
means defining a slot transversely positioned on said end portion of one of said first and second shaft means, and
a member projecting outwardly and transversely of said end portion of the other one of said first and second shaft means and being releasably engageable within said slot in response to movement of said door into said closed position only when said plate means and said control knob are each respectively positioned at generally said same relative correlated position.

8. A device according to claim 1
and further including latch means for preventing said releasable connection between said fluid control means and said control handle means, despite movement of said donor into said closed position, unless each of said fluid control means and said control handle means is mutually disposed in a particular preselected relative correlated position within said respective range of positions.

9. A device according to claim 8
wherein said latch means is further operative for locking said door in said closed position when said fluid control means which has been operatively connected with said control handle means is subsequently moved out of said particular preselected relative correlated position.

10. A device according to claim 9
wherein said control handle means includes a control knob disposed on said exterior of said door and rotatable through said range of positions associated with said control handle means, wherein said linkage means is operative for releasably connecting said control knob with said fluid control means and for thereafter transmitting rotation of said control knob into correlated movement of said fluid control means, and wherein said latch means includes
a stationary member extending from said front interior wall surface within said housing interior area toward said access opening and including a peripheral latching groove, and
disc means supported on said interior of said door and operatively connected with said control knob for common rotation therewith, said disc means being operative, when said control knob and said fluid control means are each disposed out of said particular preselected correlated position, for engagement with said stationary member out of said latching groove as said door is moved toward said closed position to thereby prevent movement of said door into said closed position and said connection between said control knob and said fluid control means; being operative, when said control knob and said fluid control means are each disposed in said particular preselected correlated position, for engagement with said stationary member releasably within said latching groove as said door is moved into said closed position to thereby permit movement of said door into said closed position and said connection between said control knob and said fluid control means; and being further operative, when said door is in said closed position and said control knob and fluid control means are connected and disposed out of said preselected correlated position, for preventing disengagement between said disc means and said latching groove to thereby lock said door in said closed position.

11. A device according to claim 1 and further including switch means adapted for connection with an electrical circuit and operatively connected with said fluid control means for controlling the flow of electricity through the circuit in response to movement of said fluid control means.

12. A device for controlling the flow of fluid through flexible collapsible conduit means, said device comprising a housing having spaced walls defining an interior area accommodating the mounting of a portion of the conduit means and including a door movable between an opening permitting access into said interior area and a closed position blocking said access, fluid control means carried within said interior area and being operative for controlling the flow of fluid through the conduit means, said fluid control means including plates means disposed in facing relationship with the conduit means, said plate means being operative for rotation through a range of positions and including a plurality of arcuate grooves concentrically arranged at radially spaced intervals outwardly of the axis of rotation of said plate means, cam means including at least one generally arcuately shaped cam member attachable to said plate means within a selected one of said arcuate grooves for movement in a generally arcuate path during rotation of said plate means, and pin means including at least one pin member associated with each of said cam members which are attached to said plate means, each of said pin members being disposed intermediate said plate means and the conduit means along said path of arcuate movement of said associated cam member for contact with said associated cam member during rotation of said plate means, each of said pin members being independently movable in response to contact by said associated cam member between the normal position and a displaced position, each of said pin members being operative during said movement from said normal position toward said displaced position for pressing against and collapsing a area of the conduit means to obstruct the flow of fluid therethrough, control handle means carried by said door and being operative for movement through a range of positions generally correlated with said range of positions of said fluid control means, and linkage means operative, when said fluid control means and said control handle means are each respectively positioned at generally the same relative correlated position within said respective range of positions, for releasable connecting said control handle means with said plate means in response to movement of said door into said closed position and, after said releasable connection has been made and said door is maintained in said closed position, for moving said fluid control means through its range of positions by rotating said plate means in response to and in relative correlation with movement of said control handle means through its range of positions.

13. A device according to claim 12 wherein said door includes an exterior facing away from said interior area of said housing when said door is in said closed position, wherein said control handle means includes a control knob disposed on said exterior of said door and rotatable through said range of positions associated with said control handle means, and wherein said linkage means is operative for releasably connecting said control knob with said plate means and for thereafter transmitting rotation of said control knob into correlated rotation of said plate means.

14. A device according to claim 13 wherein said linkage means includes first shaft means operatively connected with said plate means for common rotation therewith, and second shaft means operatively connected with said control knob for common rotation therewith, and means on said first and second shaft means operative, when said plate means and said control knob are each respectively positioned at generally said same relative correlated position, for releasably connecting said first shaft means and said second shaft means in response to movement of said door into said closed position and for thereafter moving said plate means in response to and in relative correlation with movement of said control knob.

15. A device according to claim 14 wherein said linkage means includes means defining a slot transversely positioned on said end portion of one of said first and second shaft means, and a member projecting outwardly and transversely of said end portion of the other one of said first and second shaft means and being releasably engageable within said slot in response to movement of said door into said closed position only when said plate means and said control knob are each respectively positioned at generally said same relative correlated position.

16. A device according to claim 13 and further comprising latch means including a stationary member extending within said housing interior area toward said door and including a peripheral latching groove, and disc means supported on said interior of said door and operatively connected with said control knob for common rotation therewith, said disc means being operative, when said control knob and said fluid control means are each disposed out of said particular preselected correlated position, for engagement with said stationary member out of said latching groove as said door is moved toward said closed position to thereby prevent movement of said door into said closed position and said connection between said control knob and said fluid control means; being operative, when said control knob and said fluid control means are each disposed in said particular preselected correlated position, for engagement with said stationary member releasably within said latching groove as said door is moved into said closed position to thereby permit movement of said door into said closed position and said connection between said control knob and said fluid control means; and being further operative, when said door is in said closed position and said control knob and fluid control means are connected and disposed out of said preselected correlated position, for preventing disengagement between said disc means and said latching groove to thereby lock said door in said closed position.

17. A device according to claim 12 and further including switch means adapted for connection with an electrical circuit and operatively connected with said plate means for controlling the flow of electricity through the circuit in response to rotation of said plate means.

18. A device for controlling the flow of fluid through flexible collapsible conduit means, said device comprising a housing having spaced walls defining an interior area accommodating the mounting of a portion of the conduit means and including a door movable between an open position permitting access into said interior area and a closed position blocking said access, said door including an exterior facing away from said interior area of said housing when said door is in said closed position and an interior facing toward said interior area of said housing when said door is in said closed position, fluid control means carried within said interior area and being operatively movable through a range of positions for controlling the flow of fluid through the conduit means, a control knob carried on the exterior of said door and being operative for rotation through a range of positions generally correlated with said range of positions of said fluid control means, linkage means operative, when said fluid control means and said control knob are each respectively positioned at generally the same relative correlated position within said respective range of positions, for releasable connecting said control knob with said fluid control means in response to movement of said door into said closed position and, after said releasable connection has been made and said door is maintained in said closed position, for moving said fluid control means through its range of positions in response to and in relative correlation with movement of said control knob through its range of positions, and latch means including a stationary member extending within said housing interior area toward said door and including a peripheral latching groove, and disc means supported on said interior of said door and operatively connected with said control knob for common rotation therewith, said disc means being operative, when said control knob and said fluid control means are each disposed out of said particular preselected correlated position, for engagement with said stationary member out of said latching groove as said door is moved toward said closed position to thereby prevent movement of said door into said closed position and said connection between said control knob and said fluid control means; being operative, when said control knob and said fluid control means are each disposed in said particular preselected correlated position, for engagement with said stationary member releasably within said latching groove as said door is moved into said closed position to thereby permit movement of said door into said closed position and said connection between said control knob and said fluid control means; and being further operative, when said door is in said closed position and said control knob and fluid control means are connected and disposed out of said preselected correlated position, for preventing disengagement between said disc means and said latching groove to thereby lock said door in said closed position.

19. A device according to claim 18 and further including switch means adapted for connection with an electrical circuit and operatively connected with said fluid control means for controlling the flow of electricity through the circuit in response to movement of said fluid control means.

20. A manually actuated control switch device for controlling the flow of fluid through flexible collapsible conduit means associated with a plasmapheresis assembly, said device comprising a housing having spaced walls defining an interior area accommodating the mounting of a portion of the conduit means and including a door movable between an open position permitting access into said interior area and a closed position blocking said access, fluid control means carried within said interior area for controlling the flow of fluid through the conduit means said fluid control means including plate means disposed in facing relationship with the conduit means, said plate means being operative for rotation through a range of positions, pin means disposed intermediate said plate means and the conduit means and movable between a normal position and a displaced position, said pin means being operative during said movement from said normal position toward said displaced position for pressing against and collapsing a area of the conduit means to obstruct the flow of fluid therethrough, and cam means operatively connecting said plate means with said pin means for moving said pin means between said normal and displaced positions in response to rotation of said plate means within said associated range of positions, control handle means carried by said door and being operative for movement through a range of positions generally correlated with said range of positions of said fluid control means, and linkage means operative, when said plate means and said control handle means are each respectively positioned at generally the same relative correlated position within said respective range of positions, for releasable connecting said control handle means with said plate means in response to movement of said door into said closed position and, after said releasable connection has been made and said door is maintained in said closed position, for rotating said plate means through its range of positions in response to and in relative correlation with movement of said control handle means through its range of positions.

21. A device according to claim 20
wherein said cam means includes a generally arcuately shaped cam member attachable to said plate means at a position radially outwardly spaced from the axis of rotation thereof to thereby move in a generally arcuate path during rotation of said plate means, and wherein said pin means is disposed along said path of arcuate movement of said cam member for contact with said cam member during rotation of said plate means.

22. A device according to claim 11
wherein said plate means includes a plurality of arcuate groove concentrically arranged at radially spaced intervals outwardly of the axis of rotation of said plate means, each of said grooves accommodating at least one of said cam members, and wherein said pin means includes at least one pin member associated with each of said cam members which are arcuately carried on said plate means, each of said pin members being disposed along said path of arcuate movement of said associated cam member and independently movable in response to contact by said associated cam member between said normal and displaced positions to obstruct the flow of fluid through the conduit means.

23. A device according to claim 20 or 21 or 22
wherein said door includes an exterior facing away from said interior area of said housing when said door is in said closed position, wherein said control handle means includes a control knob disposed on said exterior of said door and rotatable through said range of positions associated with said control handle means, and wherein said linkage means is operative for releasably connecting said control knob with said plate means and for thereafter transmitting rotation of said control knob into correlated rotation of said plate means.

24. A device according to claim 23 wherein said linkage means includes
first shaft means operatively connected with said plate means for common rotation therewith, and
second shaft means operatively connected with said control knob for common rotation therewith, and
means on said first and second shaft means operative, when said plate means and said control knob are each respectively positioned at generally said same relative correlated position, for releasably connecting said first shaft means and said second shaft means in response to movement of said door into said closed position and for thereafter moving said plate means in response to and in relative correlation with movement of said control knob.

25. A device according to claim 24
wherein said linkage means includes
means defining a slot transversely positioned on said end portion of one of said first and second shaft means, and
a member projecting outwardly and transversely of said end portion of the other one of said first and second shaft means and being releasably engageable within said slot in response to movement of said door into said closed position only when said plate means and said control knob are each respectively positioned at generally said same relative correlated position.

26. A device according to claim 20
and further including latch means for preventing said releasable connection between said fluid control means and said control handle means, despite movement of said door into said closed position, unless each of said fluid control means and said control handle means is mutually disposed in a particular preselected relative correlated position within said respective range of positions.

27. A device according to claim 26
wherein said latch means is further operative for locking said door in said closed position when said fluid control means which has been operatively connected with said control handle means is subsequently moved out of said particular preselected relative correlated position.

28. A device according to claim 27
wherein said door includes an exterior facing away from said interior area of said housing when said door is in said closed position and an interior facing toward said interior area of said housing when said door is in said closed position, wherein said control handle means includes a control knob disposed on said exterior of said door and rotatable through said range of positions associated with said control handle means, wherein said linkage means is operative for releasably connecting said control knob with said fluid control means and for thereafter transmitting rotation of said control knob into correlated movement of said control means, and wherein said latch means includes
a stationary member extending within said housing interior area toward said door and including a peripheral latching groove, and
disc means supported on said interior of said door and operatively connected with said control knob for common rotation therewith, said disc means being operative, when said control knob and said fluid control means are each disposed out of said particular preselected correlated position, for engagement with said stationary member out of said latching groove as said door is moved toward said closed position to thereby prevent movement of said door into said closed position and said connection between said control knob and said fluid control means; being operative, when said control knob and said fluid control means are each disposed in said particular preselected correlated position, for engagement with said stationary member releasably within said latching groove as said door is moved into said closed position to thereby permit movement of said door into said closed position and said connection between said control knob and said fluid control means; and being further operative, when said door is in said closed position and said control knob and fluid control means are connected and disposed out of said preselected correlated position, for preventing disengagement between said disc means and said latching groove to thereby lock said door in said closed position.

29. A device according to claim 20 and further including switch means adapted for connection with an electrical circuit and operatively connected with said fluid control means for controlling the flow of electricity through the circuit in response to movement of said fluid control means.

* * * * *